US00PP34816P2

(12) United States Plant Patent
Cain

(10) Patent No.: US PP34,816 P2
(45) Date of Patent: Dec. 13, 2022

(54) GRAPEVINE PLANT NAMED 'IFG FORTY-EIGHT'

(50) Latin Name: *Vitis vinifera*
Varietal Denomination: IFG Forty-eight

(71) Applicant: International Fruit Genetics, LLC, Bakersfield, CA (US)

(72) Inventor: David Cain, Lutz, FL (US)

(73) Assignee: International Fruit Genetics, LLC., Bakersfield, CA (US)

( * ) Notice: Subject to any disclaimer, the term of this patent is extended or adjusted under 35 U.S.C. 154(b) by 0 days.

(21) Appl. No.: 17/812,085

(22) Filed: Jul. 12, 2022

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 6/88
See application file for complete search history.

*Primary Examiner* — Anne Marie Grunberg

(57) ABSTRACT

This invention is a new and distinct variety of grapevine denominated 'IFG Forty-eight'. The new grapevine is characterized by producing small sized obtuse ovoid white berries having crisp texture with a strong muscat flavor and which ripens in early season. Berries are borne on medium size clusters which are loose and do not need gibberellin applications to thin clusters. Gibberellin is required to increase berry size.

1 Drawing Sheet

Latin name of the genus and species claimed: *Vitis vinifera.*

Variety denomination: 'IFG FORTY-EIGHT'.

BACKGROUND OF THE INVENTION

The new and distinct Grapevine plant described and claimed herein originated from a hand pollinated cross of 'Diamond Muscat' (USDA variety non-patented) and 'Princess' (USDA variety non-patented) hybridized in May 2004. The abortive seed traces were subsequently embryo cultured and the resulting 45 seedlings were planted in the field in April 2005. The present variety of grapevine was selected as a single plant in September 2006 and was asexually propagated by hardwood cuttings in December 2013 near Delano, Kern County, Calif. These resulting cuttings produced second generation plants that were planted during April 2014 near Delano, Kern County, Calif. and were observed for four years and found to reproduce true-to-type.

BRIEF SUMMARY OF THE INVENTION

The new grapevine 'IFG Forty-eight' is characterized by producing small sized obtuse ovoid white berries having crisp texture with a strong muscat flavor and which ripens in early season. Berries are borne on medium size clusters which are loose and do not gibberellin applications to thin clusters. Gibberellin is required to increase berry size. 'IFG Forty-eight' stores well. Stems remain green and berries retain their crisp texture and strong muscat flavor for up to eight weeks in cold storage. To the inventor's knowledge, the known variety to which the new grapevine variety is most similar is the Perlette variety (unpatented). 'IFG Forty-eight' differs from the 'Perlette' by ripening approximately two to three weeks later, and having a very strong muscat flavor as opposed to the neutral to very mild muscat flavor of 'Perlette' and by having naturally larger berries than 'Perlette'.

'IFG Forty-eight' differs from its maternal parent, 'Diamond Muscat' by producing larger, obtuse ovoid white berries as opposed to the smaller oval berries of 'Diamond Muscat'. Clusters of 'IFG Forty-eight' are larger and less compact than 'Diamond Muscat'. It differs from its pollen parent, 'Princess' by ripening about two to three weeks earlier, by having smaller natural berry size by having a stronger muscat flavor and by having more obtuse ovoid berry shape as opposed to the more cylindrical shape of 'Princess'.

BRIEF DESCRIPTION OF THE DRAWING

The accompanying photographic drawing in FIG. 1 illustrates in full color 'IFG Forty-eight'. The photograph was taken outdoors with indirect lighting. The colors are as nearly true as is reasonably possible in a color representation of this type. The left side of the drawing has a mature leaf. A mature fruit cluster is represented in the center of the drawing along with a typical berry in cross section. A young shoot tip can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2016 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 'IFG Forty-eight' plants grown in the vicinity of Delano, Kern County, Calif. during 2018 and 2019, and is believed to apply to plants of the variety grown under similar conditions of soil and climate elsewhere:

VINE

General:

*Vigor.*—Vigorous.

*Density of foliage.*—Dense.

*Productivity.*—Productive, producing about 13.1 to 19.6 kg of fruit per vine.

*Resistance/susceptibility to typical pests and disease of vitis vinifera species.*—Not observed to date.

*Plant hardiness zone.*—Fully hardy in USDA zone 9A (2012). Not tested in other zones.

*Root stock.*—Own root.

*Training method.*—Typically spur pruned leaving 2 bud spurs.

Trunk:

*Trunk diameter of* 4-*year-old vines at* 30 *cm above the soil line.*—Approximately 6.2 cm.

*Shape.*—Stocky.

*Surface texture.*—Shaggy texture.

*Inner bark color.*—Greyed-orange: 165A.

*Outer bark color.*—Brown: N200B.

SHOOTS

Young shoot:

*Form of tip.*—Fully opened.

*Distribution of anthocyanin coloration of tip.*—Absent.

*Intensity of anthocyanin coloration of tip.*—Absent.

*Density of prostrate hairs of tip.*—Very sparse.

*Density of erect hairs on tip.*—Absent.

*Color.*—Yellow-green: 144B.

Woody shoot (mature canes):

*Internode length.*—Medium: About 9.8 cm.

*Width at node.*—About 1.7 cm.

*Cross section.*—Circular.

*Surface.*—Striate.

*Main color.*—The following colors were observed: Greyed-orange: 176A and 165B and 165C.

*Density of erect hairs on nodes.*—None or very sparse.

*Density of erect hairs on internodes.*—None or very sparse.

*Axillary shoot vigor at full bloom.*—Weak: Approximately 4.2 cm long.

Flowering shoot:

*Vigor during flowering.*—Strong.

*Attitude during flowering on shoots not tied.*—Semi-erect.

*Color-dorsal side of internodes.*—Yellow-green: 144B.

*Color-ventral side of internodes.*—Yellow-green: 144B.

*Color-dorsal side of nodes.*—Yellow-green: 144B, with Red-purple stripes: 184A.

*Color-ventral side of nodes.*—Yellow-green: 144B.

*Density of prostrate hairs on nodes.*—None to very sparse.

*Density of erect hairs on nodes.*—None to very sparse.

*Density of prostrate hairs on internode.*—Very sparse.

*Density of erect hairs on internode.*—None to very sparse.

*Anthocyanin coloration of buds.*—Present.

Tendrils:

*Distribution on the shoot* (*at full flowering*).—Discontinuous.

*Length of Tendril.*—Long: About 28.4 cm.

*Thickness of tendril* 2 *cm from base.*—About 2.5 mm.

*Color.*—The following colors were observed: Yellow-green: 144A and 144B and 144C.

*Form.*—Mixture of bifurcated and trifurcated.

*Number of consecutive tendrils.*—2.

LEAVES

Young leaves:

*Color of upper surface of first four distal unfolded leaves.*—Yellow-green: 144A.

*Color of lower surface of young leaves.*—Yellow-green: 144A.

*Average intensity of anthocyanin coloration of six distal leaves prior to flowering.*—Absent or very weak.

*Density of prostrate hairs between veins* (*lower surface*).—Absent.

*Density of prostrate hairs on veins* (*lower surface*).—Very sparse.

*Density of erect hairs between veins* (*lower surface*).—Absent.

*Density of erect hairs on veins* (*lower surface*).—Absent.

Mature leaves (opposite first cluster):

*Average length.*—About 15.0 cm.

*Average width.*—About 18.0 cm.

*Mature leaf size.*—Large.

*Shape of blade.*—Wedge-shaped.

*Number of lobes.*—5.

*Blade venation.*—Palmate.

*Anthocyanin coloration of main veins on upper side of blade.*—Absent.

*Mature leaf profile.*—Undulate.

*Blistering surface of blade upper surface.*—Medium.

*Leaf blade tip.*—In the plane of the leaf.

*Leaf apex.*—Acute.

*Leaf margin.*—Serrate.

*Undulation of margin.*—Medium.

*Undulation of blade between main and lateral veins.*—Overall.

*Shape of teeth.*—Mixture of both sides straight and both sides convex.

*Length of teeth.*—About 0.4 cm.

*Width of teeth.*—About 1.1 cm.

*Ratio length/width of teeth.*—Medium.

*Shape of upper lateral sinuses.*—Lobes slightly overlapping.

*Depth of upper lateral sinuses.*—Medium.

*General shape petiole sinus.*—Slightly open.

*Shape of base of upper leaf sinuses.*—U-shaped.

*Tooth at petiole sinus.*—Absent.

*Density of prostrate hairs between veins on lower surface of blade.*—Very sparse.

*Density of erect hairs between veins on lower surface of blade.*—Absent.

*Density of prostrate hairs on main veins on lower surface of blade.*—Very sparse.

*Density of erect hairs on main veins on lower surface of blade.*—Very sparse.
*Density of prostrate hairs on main veins on upper surface of blade.*—Very sparse.
*Density of erect hairs on main veins on upper surface of blade.*—None.
*Autumn coloration of leaves.*—Leaves can be a single color or combination of colors, in a mottled pattern or on the edges of the leaves. The following colors were observe: Greyed-yellow: 162A and 162B.

Upper surface:
*Color.*—Green: 137A.
*Anthocyanin coloration of main veins* (*upper surface*).—Absent.
*Color of main veins.*—Yellow-green: 144C.
*Surface appearance.*—Glossy.
*Blistering surface of blade.*—Weak.

Lower surface:
*Color.*—Yellow-green: 146A.
*Anthocyanin coloration of main veins* (*lower surface*).—Absent.
*Color of main veins.*—Yellow-green: 145C.
*Glossiness.*—Medium.
*Surface texture.*—Smooth.
*Surface appearance.*—Semi-glossy.

Petiole:
*Length.*—About 12.8 cm.
*Diameter of petiole 2 cm from blade.*—About 3.2 mm.
*Petiole color.*—The following colors were observed: Yellow-green: 145A and Greyed-purple: 184A.
*Length of petiole compared to middle vein.*—Slightly shorter.
*Density of prostrate hairs on petiole.*—None or very sparse.
*Density of erect hairs on petiole.*—None.

Buds:
*Bud fruitfulness.*—Basal: mostly fruitful.
*Position of first fruitful shoot on previous season cane.*—$1^{st}$ to $2^{nd}$ node.
*Dormant bud length.*—About 10.5 mm.
*Dormant bud width in the proximal/distal plane.*—About 1.7 mm.
*Dormant bud color.*—Greyed-orange: 164A.
*Time of bud burst.*—Early season: About Mar. 11, 2018.

FLOWERS

General:
*Flower sex.*—Hermaphrodite.
*Length of single flower, unopened.*—About 2.8 mm.
*Width of single flower.*—Unopened: About 2.1 mm. Opened: About 6.0 mm.
*Stamen length.*—About 3.2 mm.
*Stamen count.*—5.
*Pollen color.*—Yellow: 10B.
*Pistil length.*—About 2.5 mm.
*Pistil color.*—Yellow-green: 144A.
*Length of first inflorescence.*—Medium: About 21.5 cm long by 14.4 cm wide.
*Position of first flowering and fruiting node.*—$3^{rd}$ to $5^{th}$ node (current season growth).
*Number of inflorescence per flowering shoot.*—1.1 to 2: About 2.
*Time of bloom.*—Midseason as compared with similar varieties in the growing area of Delano, Calif.
*Date of full bloom.*—About May 5, 2019.

FRUIT

General:
*Ripening period.*—Early: Approximately Jul. 18, 2018.
*Use.*—Fresh market and raisin.
*Keeping quality.*—Excellent, remains commercially acceptable when stored up to 8 weeks at 0.5° C. and high relative humidity.
*Refractometer test.*—Soluble solids: About 20.2 Brix.
*Brix/acid.*—About 25.3.
*Titratable acidity.*—About 0.80.
*Juice pH.*—About 3.9.
*Juice color.*—Yellow-green: 145C.

Cluster:
*Mature cluster length* (*peduncle excluded*).—About 24.3 cm.
*Mature cluster width.*—About 13.0 cm.
*Mature cluster weight.*—About 436.4 g.
*Bunch density.*—Loose: single berries, some pedicels visible.
*Number of berries.*—About 162.
*Form.*—Conical.

Peduncle:
*Lignification of peduncle.*—Weak.
*Diameter of peduncle.*—Approximately 0.7 cm.
*Length of peduncle.*—Short: Approximately 3.0 cm.
*Color of peduncle.*—Yellow-green: 144A.

Berry:
*Uniformity of size.*—Uniform.
*Single berry weight.*—About 3.6 g natural; to about 4.4 g when treated with gibberellic acid.
*Shape.*—Obtuse ovoid.
*Seeds.*—Contains tiny rudimentary seed traces.
*Cross section.*—Circular.
*Berry dimensions.*—Longitudinal axis: about 1.9 cm: Horizontal axis: about 1.7 cm.
*Pedicel length.*—About 9.8 mm.
*Pedicel width.*—About 1.2 mm.
*Pedicel color.*—Yellow-green: 144A.
*Berry firmness.*—Firm.
*Particular flavor.*—Muscat.
*Bloom* (*cuticular wax*).—Weak.
*Berry separation from pedicel.*—Medium.
*Skin color* (*without bloom*).—Yellow-green: N144A.
*Flesh color.*—Yellow-green: 145D.

Skin:
*Thickness.*—Medium.
*Skin toughness.*—Not notable when chewing.
*Reticulation.*—Absent.
*Tenacity.*—Tenacious to flesh.

What is claimed:

1. A new and distinct variety of grapevine as herein illustrated and described.

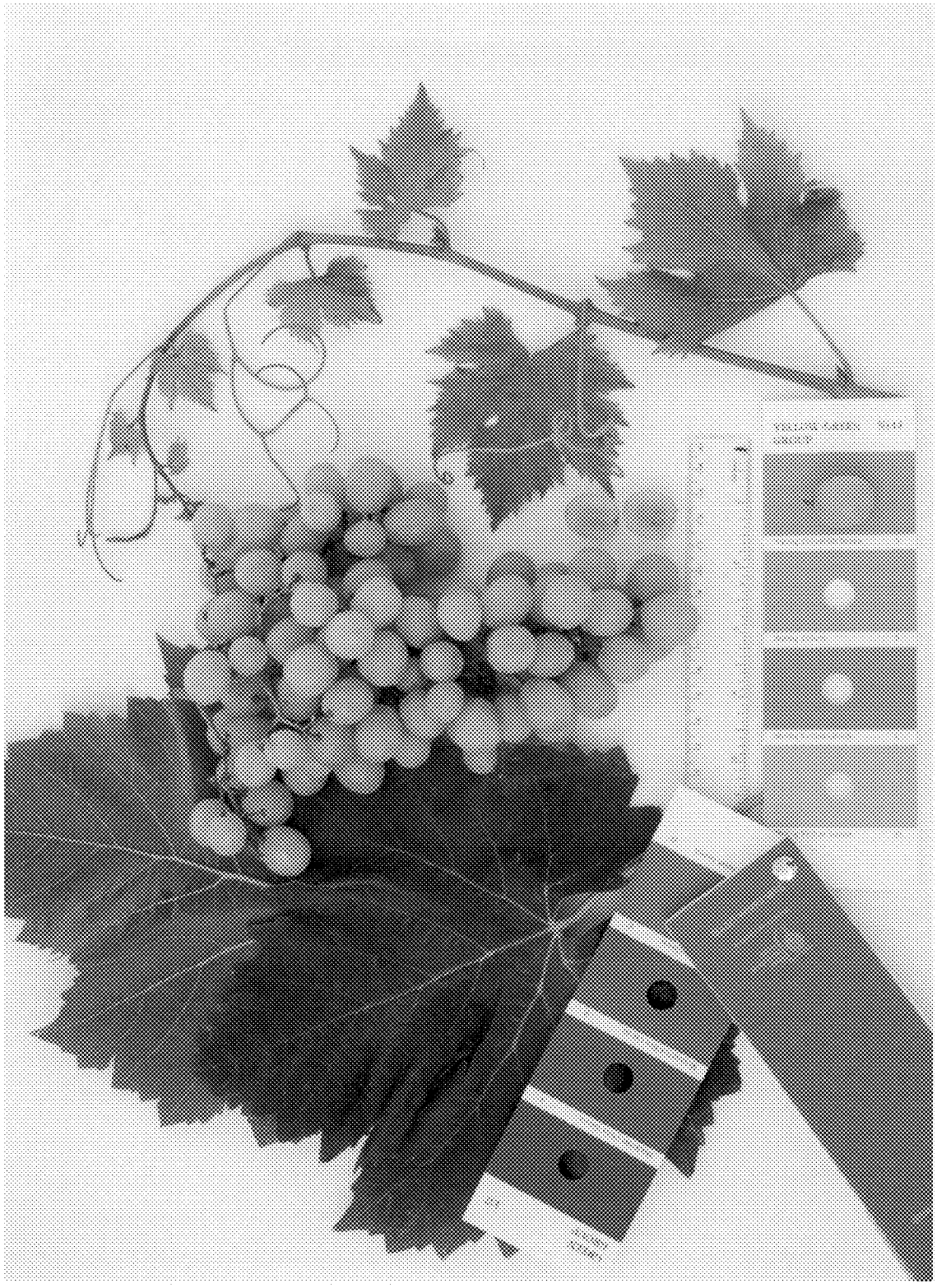

* * * * *